(12) United States Patent
Quadri

(10) Patent No.: US 11,141,265 B2
(45) Date of Patent: Oct. 12, 2021

(54) PERCUTANEOUS VALVE PROSTHESIS AND SYSTEM AND METHOD FOR IMPLANTING THE SAME

(71) Applicant: Edwards Lifesciences CardiAQ LLC, Irvine, CA (US)

(72) Inventor: Arshad Quadri, West Hartford, CT (US)

(73) Assignee: Edwards Lifesciences CardiAQ LLC, Irvine, CA (US)

(*) Notice: Subject to any disclaimer, the term of this patent is extended or adjusted under 35 U.S.C. 154(b) by 26 days.

(21) Appl. No.: 16/503,179

(22) Filed: Jul. 3, 2019

(65) Prior Publication Data

US 2019/0321174 A1    Oct. 24, 2019

Related U.S. Application Data

(63) Continuation of application No. 15/221,435, filed on Jul. 27, 2016, now Pat. No. 10,350,065, which is a
(Continued)

(51) Int. Cl.
*A61F 2/24* (2006.01)

(52) U.S. Cl.
CPC .......... *A61F 2/2418* (2013.01); *A61F 2/2436* (2013.01); *A61F 2/2439* (2013.01);
(Continued)

(58) Field of Classification Search
CPC ................................. A61F 2/24; A61F 2/2418
See application file for complete search history.

(56) References Cited

U.S. PATENT DOCUMENTS

| 3,739,402 A | 6/1973 | Cooley et al. |
| 4,079,468 A | 3/1978 | Liotta et al. |

(Continued)

FOREIGN PATENT DOCUMENTS

| CA | 2827556 A1 | 7/2012 |
| DE | 102006052564 B3 | 12/2007 |

(Continued)

OTHER PUBLICATIONS

Boujemline, Younes, et al., "Steps Toward the Percutaneous Replacement of Atrioventricular Valves," JACC, vol. 46, No. 2, Jul. 19, 2005:360-5.

(Continued)

*Primary Examiner* — Matthew W Schall
(74) *Attorney, Agent, or Firm* — Guy Cumberbatch

(57) ABSTRACT

A method for delivering a heart valve prosthesis to a native valve annulus comprises expanding an expandable frame at the native valve annulus and positioning a replacement heart valve within the expandable frame. The expandable frame preferably includes a first anchoring portion that is positioned on a first side of the native valve annulus and a second anchoring portion that is positioned on a second side of the native valve annulus. The first anchoring portion engages tissue on the first side of the native valve annulus and the second anchoring portion engages tissue on the second side of the native valve annulus for securing the expandable frame to the native valve annulus. The replacement heart valve comprises a plurality of leaflets for replacing the function of the native valve.

19 Claims, 15 Drawing Sheets

Related U.S. Application Data continuation of application No. 12/309,680, filed as application No. PCT/US2007/016855 on Jul. 27, 2007, now abandoned.

(60) Provisional application No. 60/833,791, filed on Jul. 28, 2006.

(52) U.S. Cl.
CPC ............... *A61F 2220/0016* (2013.01); *A61F 2230/0054* (2013.01); *A61F 2250/006* (2013.01)

(56) References Cited

U.S. PATENT DOCUMENTS

| | | |
|---|---|---|
| 4,339,831 A | 7/1982 | Johnson |
| 4,340,977 A | 7/1982 | Brownlee et al. |
| 4,470,157 A | 9/1984 | Love |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,458,153 B1 | 10/2002 | Bailey et al. |
| 6,582,462 B1 | 6/2003 | Andersen et al. |
| 6,610,088 B1 | 8/2003 | Gabbay |
| 6,652,578 B2 | 11/2003 | Bailey et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,875,231 B2 | 4/2005 | Anduiza et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,824,443 B2 | 11/2010 | Salahieh et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Look et al. |
| 8,070,802 B2 | 12/2011 | Lamphere et al. |
| 8,075,615 B2 | 12/2011 | Eberhardt et al. |
| 8,092,520 B2 | 1/2012 | Quadri |
| 8,118,866 B2 | 2/2012 | Herrmann et al. |
| 8,136,218 B2 | 3/2012 | Millwee et al. |
| 8,157,852 B2 | 4/2012 | Bloom et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,323,335 B2 | 12/2012 | Rowe et al. |
| 8,403,983 B2 | 3/2013 | Quadri et al. |
| 8,414,644 B2 | 4/2013 | Quadri et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,523 B2 | 7/2013 | Duffy |
| 8,479,380 B2 | 7/2013 | Malewicz et al. |
| 8,500,733 B2 | 8/2013 | Watson |
| 8,500,798 B2 | 8/2013 | Rowe et al. |
| 8,518,096 B2 | 8/2013 | Nelson |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |
| 8,617,236 B2 | 12/2013 | Paul et al. |
| 8,652,145 B2 | 2/2014 | Maimon et al. |
| 8,652,202 B2 | 2/2014 | Alon et al. |
| 8,652,203 B2 | 2/2014 | Quadri et al. |
| 8,668,733 B2 | 3/2014 | Haug et al. |
| 8,673,000 B2 | 3/2014 | Tabor et al. |
| 8,679,174 B2 | 3/2014 | Ottma et al. |
| 8,679,404 B2 | 3/2014 | Liburd et al. |
| 8,721,708 B2 | 5/2014 | Seguin et al. |
| 8,721,714 B2 | 5/2014 | Kelley |
| 8,728,155 B2 | 5/2014 | Montorfano et al. |
| 8,747,459 B2 | 6/2014 | Nguyen et al. |
| 8,747,460 B2 | 6/2014 | Tuval et al. |
| 8,758,432 B2 | 6/2014 | Solem |
| 8,764,818 B2 | 7/2014 | Gregg |
| 8,771,345 B2 | 7/2014 | Tuval et al. |
| 8,771,346 B2 | 7/2014 | Tuval et al. |
| 8,778,020 B2 | 7/2014 | Gregg et al. |
| 8,784,337 B2 | 7/2014 | Voeller et al. |
| 8,784,478 B2 | 7/2014 | Tuval et al. |
| 8,790,387 B2 | 7/2014 | Nguyen et al. |
| 8,795,356 B2 | 8/2014 | Quadri et al. |
| 8,795,357 B2 | 8/2014 | Yohanan et al. |
| 8,828,078 B2 | 9/2014 | Salahieh et al. |
| 8,828,079 B2 | 9/2014 | Thielen et al. |
| 8,834,564 B2 | 9/2014 | Tuval et al. |
| 8,858,620 B2 | 10/2014 | Salahieh et al. |
| 8,870,948 B1 | 10/2014 | Erzberger et al. |
| 8,876,894 B2 | 11/2014 | Tuval et al. |
| 8,876,895 B2 | 11/2014 | Tuval et al. |
| 8,911,455 B2 | 12/2014 | Quadri et al. |
| 8,939,960 B2 | 1/2015 | Rosenman et al. |
| 8,945,209 B2 | 2/2015 | Bonyuet et al. |
| 8,951,299 B2 | 2/2015 | Paul et al. |
| 8,992,608 B2 | 3/2015 | Haug et al. |

(56) References Cited

U.S. PATENT DOCUMENTS

| | | |
|---|---|---|
| 8,998,979 B2 | 4/2015 | Seguin et al. |
| 9,005,273 B2 | 4/2015 | Salahieh et al. |
| 9,011,521 B2 | 4/2015 | Haug et al. |
| 9,028,545 B2 | 5/2015 | Taylor |
| 9,055,937 B2 | 6/2015 | Rowe et al. |
| 9,078,749 B2 | 7/2015 | Lutter et al. |
| 9,084,676 B2 | 7/2015 | Chau et al. |
| 9,125,738 B2 | 9/2015 | Figulla et al. |
| 9,138,312 B2 | 9/2015 | Tuval et al. |
| 9,161,834 B2 | 10/2015 | Taylor et al. |
| 9,173,737 B2 | 11/2015 | Hill et al. |
| 9,180,004 B2 | 11/2015 | Alkhatib |
| 9,277,990 B2 | 3/2016 | Klima et al. |
| 9,277,993 B2 | 3/2016 | Gamarra et al. |
| 9,295,551 B2 | 3/2016 | Straubinger et al. |
| 9,326,815 B2 | 5/2016 | Watson |
| 9,331,328 B2 | 5/2016 | Eberhardt et al. |
| 9,339,382 B2 | 5/2016 | Tabor et al. |
| 9,445,897 B2 | 9/2016 | Bishop et al. |
| 9,456,877 B2 | 10/2016 | Weitzner et al. |
| 9,681,968 B2 | 6/2017 | Goetz et al. |
| 9,700,329 B2 | 7/2017 | Metzger et al. |
| 9,700,411 B2 | 7/2017 | Klima et al. |
| 9,795,479 B2 | 10/2017 | Lim |
| 9,833,313 B2 | 12/2017 | Board et al. |
| 9,861,473 B2 | 1/2018 | Lafontaine |
| 9,861,476 B2 | 1/2018 | Salahieh et al. |
| 9,861,477 B2 | 1/2018 | Backus et al. |
| 9,867,698 B2 | 1/2018 | Kovalsky et al. |
| 9,877,830 B2 | 1/2018 | Lim et al. |
| 9,889,029 B2 | 2/2018 | Li et al. |
| 9,895,225 B2 | 2/2018 | Rolando et al. |
| 9,925,045 B2 | 3/2018 | Creaven et al. |
| 2001/0007956 A1 | 7/2001 | Letac et al. |
| 2002/0032481 A1 | 3/2002 | Gabbay |
| 2004/0117009 A1 | 6/2004 | Cali et al. |
| 2004/0210304 A1 | 10/2004 | Seguin et al. |
| 2005/0033398 A1 | 2/2005 | Seguin |
| 2005/0075727 A1 | 4/2005 | Wheatley |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0074484 A1* | 4/2006 | Huber .................... A61F 2/013 623/2.11 |
| 2006/0173537 A1 | 8/2006 | Yang et al. |
| 2006/0212110 A1 | 9/2006 | Osborne et al. |
| 2006/0241745 A1 | 10/2006 | Solem |
| 2006/0253191 A1 | 11/2006 | Salahieh et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0255394 A1 | 11/2007 | Ryan |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0147183 A1 | 6/2008 | Styrc |
| 2008/0161911 A1 | 7/2008 | Revuelta et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0171456 A1 | 7/2009 | Kveen et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0292350 A1 | 11/2009 | Eberhardt et al. |
| 2009/0306768 A1 | 12/2009 | Quadri |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0305685 A1 | 12/2010 | Millwee et al. |
| 2011/0004296 A1 | 1/2011 | Lutter et al. |
| 2011/0224785 A1 | 9/2011 | Hacohen |
| 2011/0264196 A1 | 10/2011 | Savage et al. |
| 2011/0313515 A1 | 12/2011 | Quadri et al. |
| 2012/0022639 A1 | 1/2012 | Hacohen et al. |
| 2012/0041550 A1 | 2/2012 | Salahieh et al. |
| 2012/0059454 A1 | 3/2012 | Millwee et al. |
| 2012/0078360 A1 | 3/2012 | Rafiee |
| 2012/0101572 A1 | 4/2012 | Kovalsky et al. |
| 2012/0123529 A1 | 5/2012 | Levi et al. |
| 2012/0215303 A1 | 8/2012 | Quadri et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0053950 A1 | 2/2013 | Rowe et al. |
| 2013/0131788 A1 | 5/2013 | Quadri et al. |
| 2013/0144378 A1 | 6/2013 | Quadri et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0194981 A1 | 7/2014 | Menk et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0222136 A1 | 8/2014 | Geist et al. |
| 2014/0222139 A1 | 8/2014 | Nguyen et al. |
| 2014/0277390 A1 | 9/2014 | Ratz et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0336754 A1 | 11/2014 | Gurskis et al. |
| 2014/0343670 A1 | 11/2014 | Bakis et al. |
| 2014/0343671 A1 | 11/2014 | Yohanan et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371847 A1 | 12/2014 | Madrid et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0012085 A1 | 1/2015 | Salahieh et al. |
| 2015/0018944 A1 | 1/2015 | O'Connell et al. |
| 2015/0039083 A1 | 2/2015 | Rafiee |
| 2015/0148731 A1 | 5/2015 | Mcnamara et al. |
| 2015/0157457 A1 | 6/2015 | Hacohen |
| 2015/0297346 A1 | 10/2015 | Duffy et al. |
| 2015/0327994 A1 | 11/2015 | Morriss et al. |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |

(56) References Cited

U.S. PATENT DOCUMENTS

| | | |
|---|---|---|
| 2016/0279386 A1 | 9/2016 | Dale et al. |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0055636 A1 | 3/2018 | Valencia et al. |
| 2018/0085218 A1 | 3/2018 | Eidenschink |
| 2018/0110534 A1 | 4/2018 | Gavala et al. |

FOREIGN PATENT DOCUMENTS

| | | |
|---|---|---|
| EP | 1171059 A1 | 1/2002 |
| EP | 1369098 A1 | 12/2003 |
| EP | 1255510 B1 | 4/2007 |
| EP | 1827558 A2 | 9/2007 |
| EP | 1239901 B1 | 10/2007 |
| EP | 1935377 B1 | 3/2010 |
| EP | 2237746 A2 | 10/2010 |
| EP | 2238947 A2 | 10/2010 |
| EP | 2398543 A1 | 12/2011 |
| EP | 1281375 B1 | 2/2012 |
| EP | 2745805 A1 | 6/2014 |
| EP | 2749254 A1 | 7/2014 |
| EP | 2750630 A1 | 7/2014 |
| EP | 2777617 A1 | 9/2014 |
| EP | 2967858 A2 | 1/2016 |
| EP | 2926766 B1 | 2/2016 |
| EP | 2985006 A1 | 2/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 2398245 A | 8/2004 |
| WO | 9749355 A1 | 12/1997 |
| WO | 2004030569 A2 | 4/2004 |
| WO | 2005011534 A1 | 2/2005 |
| WO | 2006127765 A1 | 11/2006 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2009026563 A2 | 2/2009 |
| WO | 2009033469 A1 | 3/2009 |
| WO | 2009091509 A1 | 7/2009 |
| WO | 2009134701 A2 | 11/2009 |
| WO | 2010005524 A2 | 1/2010 |
| WO | 2010022138 A2 | 2/2010 |
| WO | 2010037141 A1 | 4/2010 |
| WO | 2010040009 A1 | 4/2010 |
| WO | 2011111047 A2 | 9/2011 |
| WO | 2012177942 A2 | 12/2012 |
| WO | 2014110171 A2 | 7/2014 |
| WO | 2014210124 A1 | 12/2014 |

OTHER PUBLICATIONS

Condado, Jose Antonio, et al., "Percutaneous Treatment of Heart Valves," Rev Esp Cardio. 2006;59(12):1225-31, Applicant believes this may have been available as early as Dec. 2006.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Ma, Liang, et al., "Double-Crowned Valved Stents For Off-Pump Mitral Valve Replacement," European Journal of Cardio-thoracic Surgery 28 (2005) 194-199, Applicant believes this may have been available as early as Aug. 2005.

Pluth, James R., M.D., et al., "Aortic and Mitral Valve Replacement with Cloth-Covered Braunwald-Cutter Prosthesis, A Three-Year Follow-up," The Annals Of Thoracic Surgery, vol. 20, No. 3, Sep. 1975, pp. 239-248.

Seidel, Wolfgang, et al., "A Mitral Valve Prosthesis and a Study of Thrombosis on Heart Valves in Dogs," JSR—vol. II, No. 3—May, 1962, submitted for publication Oct. 9, 1961.

\* cited by examiner

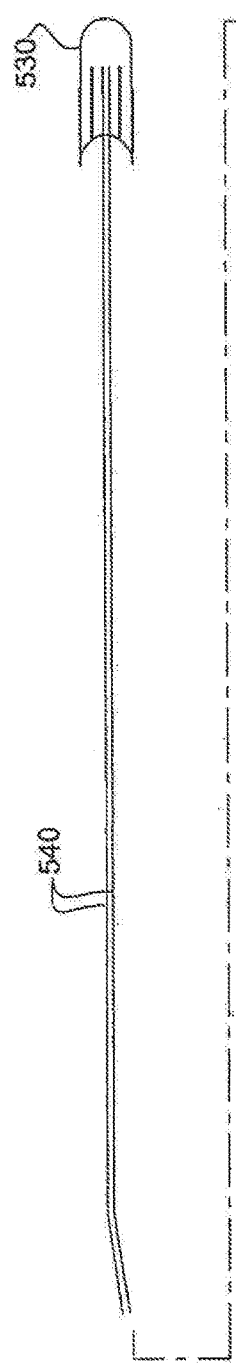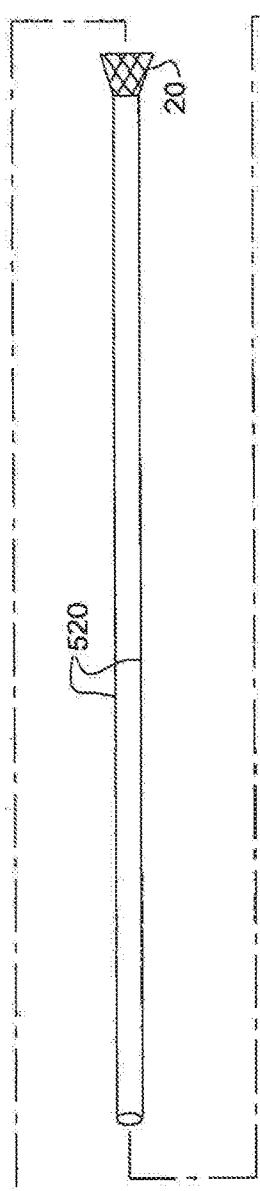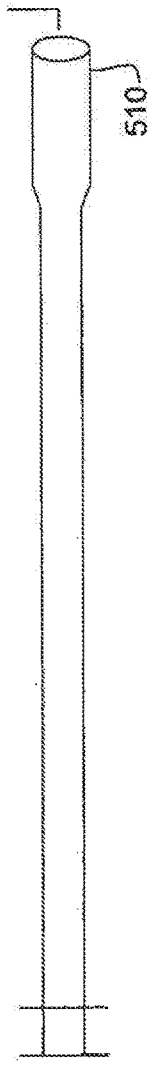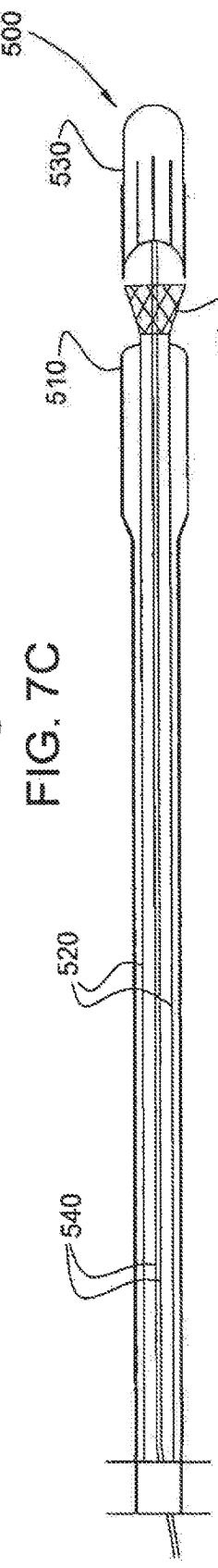
FIG. 7A
FIG. 7C
FIG. 7B

PERCUTANEOUS VALVE PROSTHESIS AND SYSTEM AND METHOD FOR IMPLANTING THE SAME

CROSS-REFERENCE TO RELATED APPLICATIONS

This application is a continuation of U.S. application Ser. No. 15/221,435, filed Jul. 27, 2016, now U.S. Pat. No. 10,350,065, which is a continuation of U.S. application Ser. No. 12/309,680, filed Aug. 20, 2009, now abandoned, which is a national stage entry of International Application No. PCT/US2007/016855, filed Jul. 27, 2007, which designates the United States and was published in English by the International Bureau on Jan. 31, 2008 as WO 2008/013915, which claims the benefit of U.S. Provisional Application No. 60/833,791, filed Jul. 28, 2006, which is incorporated herein by reference in its entirety.

BACKGROUND OF THE INVENTION

Field of the Invention

The present invention relates to heart valve prostheses, preferably to aortic valve prostheses. More specifically, the invention relates to heart valve prostheses that can be implanted percutaneously by means of a catheter from a remote location without opening the chest cavity.

Related Art

Heart valve surgery is used to repair or replace diseased heart valves. Valve surgery is an open-heart procedure conducted under general anesthesia. An incision is made through the patient's sternum (sternotomy), and the patient's heart is stopped while blood flow is rerouted through a heart-lung bypass machine.

Valve replacement may be indicated when there is a narrowing of the native heart valve, commonly referred to as stenosis, or when the native valve leaks or regurgitates. When replacing the valve, the native valve is excised and replaced with either a biologic or a mechanical valve. Mechanical valves require lifelong anticoagulant medication to prevent clot formation around the valve, which can lead to thromboembolic complications and catastrophic valve failure. Biologic tissue valves typically do not require such medication. Tissue valves can be obtained from cadavers (homografts) or can be from pigs (porcine valve) and cows (bovine pericardial valves). Recently equine pericardium has also been used for making valves. These valves are designed to be attached to the patient using a standard surgical technique.

Valve replacement surgery is a highly invasive operation with significant concomitant risk. Risks include bleeding, infection, stroke, heart attack, arrhythmia, renal failure, and adverse reactions to the anesthesia medications, as well as sudden death. Two to five percent of patients die during surgery.

Post-surgery, patients temporarily may be confused due to emboli and other factors associated with the heart-lung machine. The first two to three days following surgery are spent in an intensive care unit where heart functions can be closely monitored. The average hospital stay is between one and two weeks, with several more weeks to months required for complete recovery.

In recent years, advancements in minimally invasive, endoaortic, surgery interventional cardiology, and intervention radiology have encouraged some investigators to pursue percutaneous replacement of the aortic heart valve. Percutaneous Valve Technologies ("PVT") of Fort Lee, N.J., has developed a balloon-expandable stent integrated with a bioprosthetic valve, which is the subject of U.S. Pat. Nos. 5,411,552, 5,840,081, 6,168,614, and 6,582,462 to Anderson et al. The stent/valve device is deployed across the native diseased valve to permanently hold the valve open, thereby alleviating a need to excise the native valve and to position the bioprosthetic valve in place of the native valve. PVT's device is designed for delivery in a cardiac catheterization laboratory under local anesthesia using fluoroscopic guidance, thereby avoiding general anesthesia and open-heart surgery. The device was first implanted in a patient in April of 2002.

PVT's device suffers from several drawbacks. Deployment of PVT's stent has several drawbacks, including that there is very little control over its deployment. This lack of control can endanger the coronary ostea above the aortic valve and the anterior leaflet of the mitral valve below the aortic valve.

Another drawback of the PVT device is its relatively large cross-sectional delivery profile. This is largely due to fabricating the tri-leaflet pericardial valve inside a robust stainless steel stent. Considering they have to be durable, the materials for the valve and the stent are very bulky, thus increasing the profile of the device. The PVT system's stent/valve combination is mounted onto a delivery balloon, making retrograde delivery through the aorta challenging. An antegrade transseptal approach may therefore be needed, requiring puncture of the septum and routing through the mitral valve, which significantly increases complexity and risk of the procedure. Very few cardiologists are currently trained in performing a transseptal puncture, which is a challenging procedure by itself.

Another drawback of the PVT device is its lack of fixation provision. It in effect uses its radial force to hold the stent in the desired position. For this to work, sufficient dilatation of the valve area has to be achieved; but this amount of dilation can cause damage to the annulus. Also, due to its inability to have an active fixation mechanism, the PVT device cannot be used to treat aortic regurgitation.

Another drawback to this system is that it does not address the leakage of blood around the implant, after its implantation.

Other prior art replacement heart valves use self-expanding stents that incorporate a valve. One such device is that disclosed in U.S. Pat. No. 7,018,406 to Seguin et al. and assigned to and made by CoreValve SA. In the endovascular aortic valve replacement procedure, accurate placement of aortic valves relative to coronary ostia and the mitral valve is critical. Standard self-expanding systems have very poor accuracy in deployment, however. Often the proximal end of the stent is not released from the delivery system until accurate placement is verified by fluoroscopy and the stent typically jumps once released. It is therefore often impossible to know where the ends of the stent will be with respect to the native valve, the coronary ostia, and the mitral valve. The anchoring mechanism is not actively provided (that is, there is no method of fixation other than the use of radial force and barbs that project into the surrounding tissue and not used as positioning marker (that is, markers seen under fluoroscopy to determine the position of the device).

A simple barb as used in the CoreValve device relies mainly on friction for holding the position.

Another drawback of prior art self-expanding replacement heart valve systems is their lack of radial strength. In order for self-expanding systems to be easily delivered through a delivery sheath, the metal needs to flex and bend inside the delivery catheter without being plastically deformed. In arterial stents, this is not a challenge, and there are many commercial arterial stent systems that apply adequate radial force against the vessel wall and yet can collapse to a small enough of a diameter to fit inside a delivery catheter without plastically deforming. However, when the stent has a valve fastened inside it, as is the case in aortic valve replacement, the anchoring of the stent to vessel walls is significantly challenged during diastole. The force required to hold back arterial pressure and prevent blood from going back inside the ventricle during diastole will be directly transferred to the stent/vessel wall interface. Therefore the amount of radial force required to keep the self expanding stent/valve in contact with the vessel wall and prevent it from sliding will be much higher than in stents that do not have valves inside of them. Moreover, a self-expanding stent without sufficient radial force will end up dilating and contracting with each heartbeat, thereby distorting the valve, affecting its function and resulting in dynamic repositioning of the stent during delivery. Stent foreshortening or migration during expansion may lead to improper alignment.

Additionally, the stent disclosed in U.S. Pat. No. 6,425,916 to Garrison simply crushes the native valve leaflets against the heart wall and does not engage the leaflets in a manner that would provide positive registration of the device relative to the native position of the valve. This increases an immediate risk of blocking the coronary ostia, as well as a longer-term risk of migration of the device post-implantation. Further still, the stent comprises openings or gaps in which the replacement valve is seated post-delivery. Tissue may protrude through these gaps, thereby increasing a risk of improper seating of the valve within the stent.

In view of drawbacks associated with previously known techniques for endovascularly replacing a heart valve, it would be desirable to provide methods and apparatus that overcome those drawbacks.

Sadra et al. (U.S. published application No. 20050137701) describes a mechanism for anchoring a heart valve, the anchoring mechanism having an actuation system operated remotely. This mechanism addresses the fixation issue; however, considering the irregular shape of the aortic annulus there is a real potential for deforming the prosthetic valve annulus; this may require additional balloon angioplasty to give it its final shape, and also make the new valve more prone to fatigue and fracture. Moreover if full expansion of the stent is prone to deformation, the leaflet coaptation of the valve will be jeopardized.

Sadra et al. (U.S. published application No. 20050137691) describes a system with two pieces, a valve piece and an anchor piece. The valve piece connects to the anchor piece in such a fashion that it will reduce the effective valve area considerably. Valve area, i.e., the inner diameter of the channel after the valve leaflets open, is of prime importance when considering an aortic valve replacement in a stenotic valve. Garrison's valve is also implanted in the inner portion of the stent, compromising the effective valve outflow area. Sadra et al.'s and Garrison's valves overlook this very critically important requirement.

The technologies described above and other technologies (for example, those disclosed in U.S. Pat. No. 4,908,028 to Colon et al.; U.S. Published Application No. 2003/0014104, U.S. Published Application No. 2003/0109924, U.S. Published Application No. 2005/0251251, U.S. Published Application No. 2005/0203616, and U.S. Pat. No. 6,908,481 to Cribier; U.S. Pat. No. 5,607,469 to Frey; U.S. Pat. No. 6,723,123 to Kazatchkov et al.; Germany Patent No. DE 3,128,704 A1 to Kuepper; U.S. Pat. No. 3,312,237 to Mon et al.; U.S. Published Application No. 2005/0182483 to Osbourne et al.; U.S. Pat. No. 1,306,391 to Romanoff; U.S. Published Application No. 2005/0203618 to Sharkcawy et al.; U.S. Published Application No. 2006/0052802 to Sterman et al.; U.S. Pat. Nos. 5,713,952; and 5,876,437 to Vanney et al.) also use various biological, or other synthetic materials for fabrication of the prosthetic valve. The duration of function and physical deterioration of these new valves have not been addressed. Their changeability has not been addressed, in the percutaneous situation.

It is to the solution of these and other problems that the present invention is directed.

SUMMARY OF THE INVENTION

It is accordingly a primary object of the present invention to provide to methods and apparatus for endovascularly replacing a heart valve.

In is another object of the present invention to provide methods and apparatus for endovascularly replacing a heart valve with a replacement valve prosthesis using a balloon expandable and/or self expanding valve cage stent upon which a bi-leaflet or tri-leaflet elastic valve is inserted.

It is also a feature of this invention that the valve piece of the implant is removable, and thus exchangeable, in the event of long or medium term failure of the implanted valve.

It is another object of this invention to provide maximal valve area to the out flow tract of the left ventricle, thus minimizing the gradient across the valve, by using a supra annular implant of the valve piece to the valve cage stent.

These and other objects are achieved by a heart valve prosthesis comprising a cylindrical valve cage stent constructed to be implanted percutaneously in the planar axis of a native valve annulus, the valve cage stent having a superior rim; and an elastic and compressible, multi-leaflet valve insertable percutaneously into the body, the valve including a valve frame made from a memory metal and a tissue cover attached to the valve frame; and attachment means for attaching the valve to the superior rim of the valve cage.

The valve can be a bi-leaflet or a tri-leaflet valve. The bi-leaflet valve includes a frame, a tissue cover, a deformable hinge, and means for detachably connecting the valve to the valve cage stent. The frame has two substantially semicircular, expandable, and compressible parts, and the tissue cover is configured to cover the two parts of the frame with the straight sides of the two parts in spaced-apart relation. The tissue cover has a central aperture and the two parts of the frame have respective slots. The deformable hinge has oppositely extending arms extending through the slots and a stem received through the aperture. The superior rim of the valve cage stent has a valve mount affixed thereto for receiving a mating part on the hinge, thereby defining the attachment means.

The tri-leaflet valve includes a frame, a tissue cover, and means for detachably connecting the valve to the valve cage stent. The frame is cylindrical and has three commissural posts mounted thereon. The tissue cover has three cusps fitted and sewn to the valve frame, the commissural posts being sized to maintain the commissural height of the cusps. The valve cage stent has three commissural pins extending from the superior rim thereof, and the commissural posts of the frame are cannulated to receive the commissural pins of the valve cage stent, thereby defining the attachment means.

Other objects, features and advantages of the present invention will be apparent to those skilled in the art upon a reading of this specification including the accompanying drawings.

BRIEF DESCRIPTION OF THE DRAWINGS

The invention is better understood by reading the following Detailed Description of the Preferred Embodiments with reference to the accompanying drawing figures, in which like reference numerals refer to like elements throughout, and in which:

FIGS. 7A and 7B are exploded and assembled views, respectively, of the delivery system apparatus used in implantation of the bi-leaflet and tri-leaflet valves in accordance with the present invention.

FIG. 7C is an end view of the flexible sheath of the delivery system apparatus of FIGS. 7A and 7B.

DETAILED DESCRIPTION OF THE PREFERRED EMBODIMENTS

Figure 1:
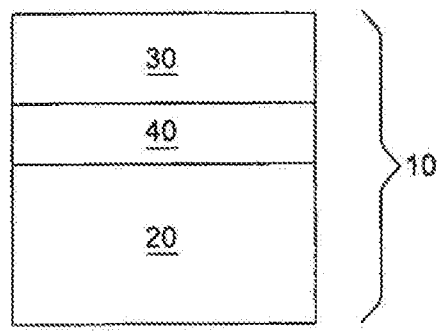
FIG. 1 is a diagram of a valve prosthesis in accordance with the present invention.

In describing preferred embodiments of the present invention illustrated in the drawings, specific terminology is employed for the sake of clarity. However, the invention is not intended to be limited to the specific terminology so selected, and it is to be understood that each specific element includes all technical equivalents that operate in a similar manner to accomplish a similar purpose.

The present invention relates to heart valve prostheses that can be implanted percutaneously by means of a catheter from a remote location without opening the chest cavity. As shown in FIG. 1, the valve prosthesis 10 comprises two parts, (1) a valve cage stent 20 constructed to be implanted in the planar axis of the native valve annulus, (2) an elastic and compressible valve 30, and (3) an attachment mechanism for attaching the valve 30 to the superior rim of the above mentioned valve cage stent 20. In accordance with the present invention, two types 110 and 210 of heart valve prosthesis 10 are contemplated, one type 110 incorporating an elastic and compressible bi-leaflet hinged valve 130 (shown in FIGS. 2A-2E) and the other type 210 incorporating an elastic and compressible tri-leaflet biologic valve 230 (shown in FIGS. 3A-3C). A system and method for implanting the valves (shown in FIGS. 4A-4G, 5A-5I, and 6A-6J) is also encompassed by the invention.

Figure 2A:
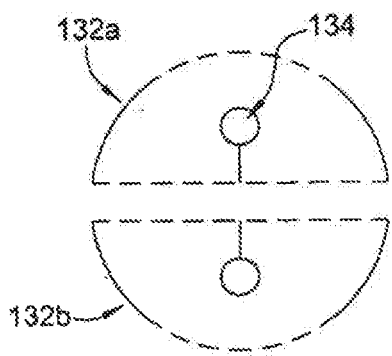
FIG. 2A is a diagrammatic plan view of a frame for a bi-leaflet percutaneous heart valve in accordance with the present invention.
Figure 2B:
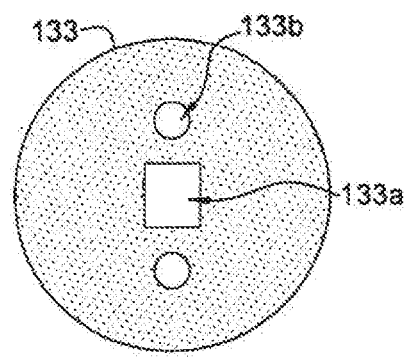
FIG. 2B is a diagrammatic plan view of a tissue cover for the frame of FIG. 2A.
Figure 2C:
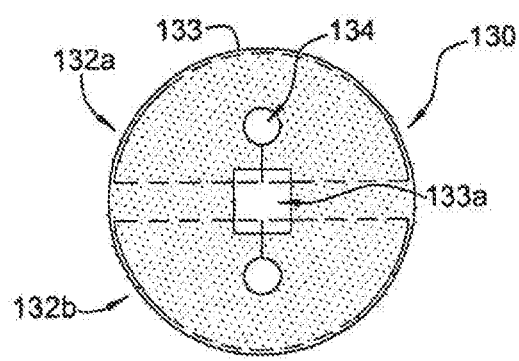
FIG. 2C is a diagrammatic plan view of an assembled bi-leaflet percutaneous heart valve in accordance with the present invention, incorporating the frame of FIG. 2A and the tissue cover of FIG. 2B.

Referring now to FIGS. 2A-2H, the bi-leaflet tissue valve 130 comprises a two-part (that is, a two-leaflet) frame 132 made from a memory metal wire or strip and a tissue cover 133. As best shown in FIG. 2A, each part 132*a* and 132*b* of the frame 132 is substantially semicircular. Portions of each part 132*a* and 132*b* of the frame 132 (for example, the straight side and the center portion of the curved side) are configured (for example, by having a sinusoidal configuration, shown by broken lines in FIGS. 2A and 2C) so that each part 132*a* and 132*b* of the frame 132, as well as the frame 132 as a whole, is expandable and compressible, while the remaining portions of the frame 132 are not expandable and compressible.

Figure 2D:
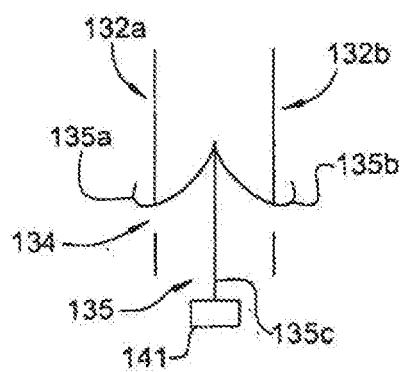
FIG. 2D is a diagrammatic side elevational view of the bi-leaflet percutaneous heart valve of FIG. 2C in the open position.
Figure 2E:
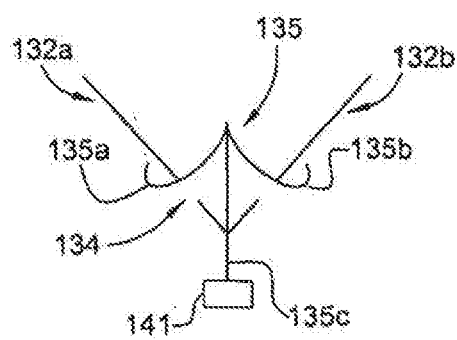
FIG. 2E is a diagrammatic side elevational view of the bi-leaflet percutaneous heart valve of FIG. 2C in the closed position.
Figure 2F:
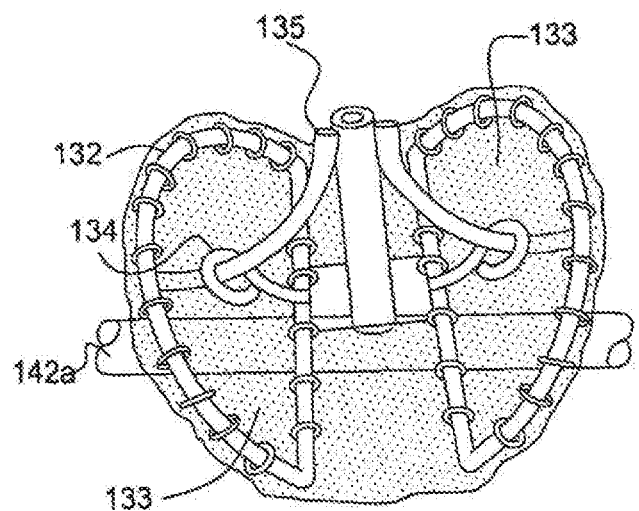
FIG. 2F is a top perspective view of an assembled bi-leaflet percutaneous heart valve in accordance with the present invention, in the closed position.
Figure 2G:
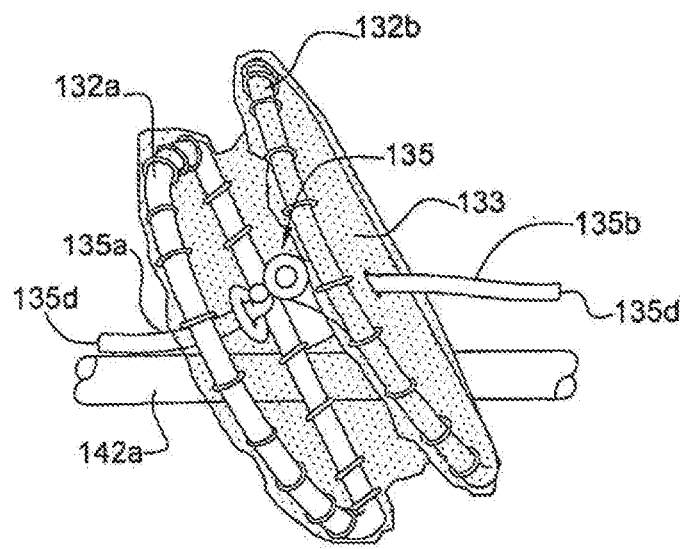
FIGS. 2G and 2H are top and side perspective views of the bi-leaflet percutaneous heart valve of FIG. 2F in the open position.
Figure 2H:
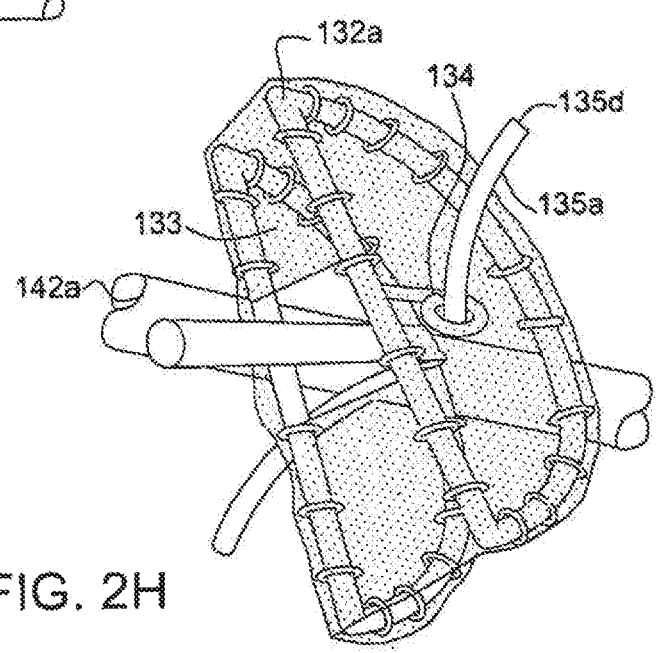
Figure 2I:
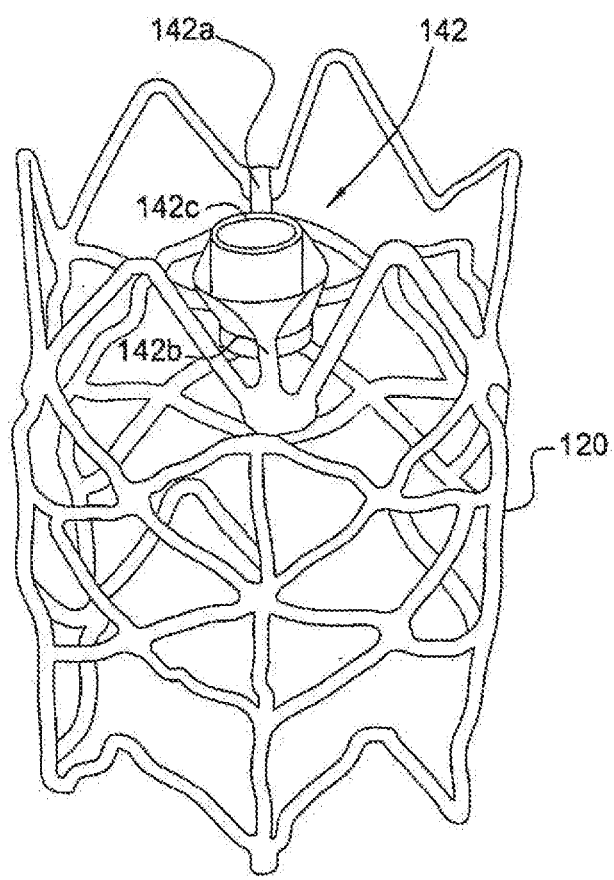
FIGS. 2I and 2J are side perspective views of the valve cage stent for use with the bi-leaflet percutaneous heart valve of FIG. 2F.
Figure 2J:
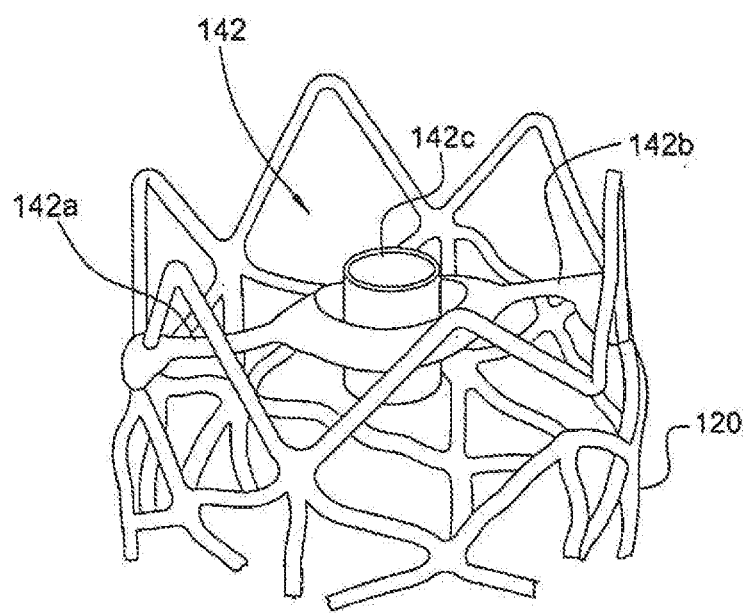
Figure 2K:
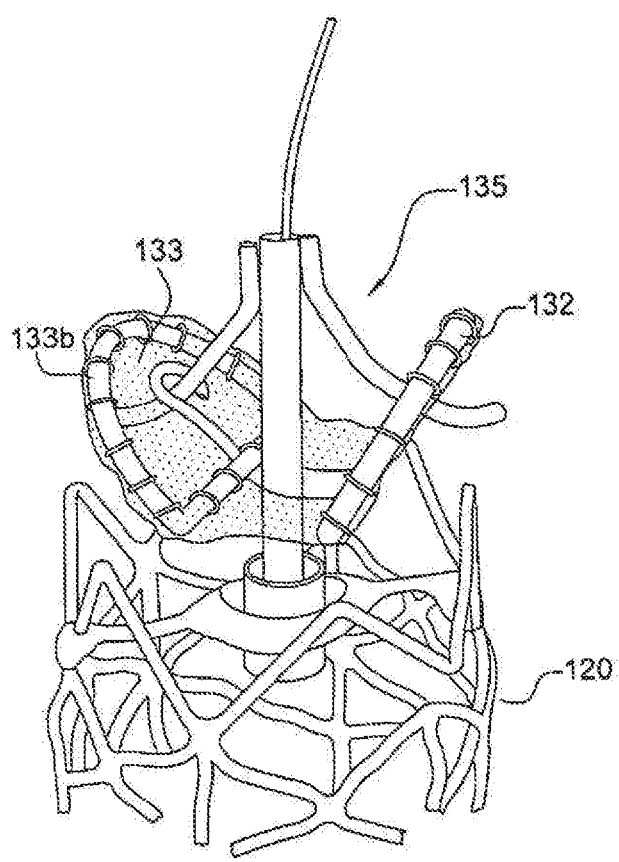
FIG. 2K is a partial perspective view of the bi-leaflet percutaneous heart valve of FIG. 2F mounted on the valve cage stent of FIG. 2I, with the valve in the closed position.
Figure 2L:
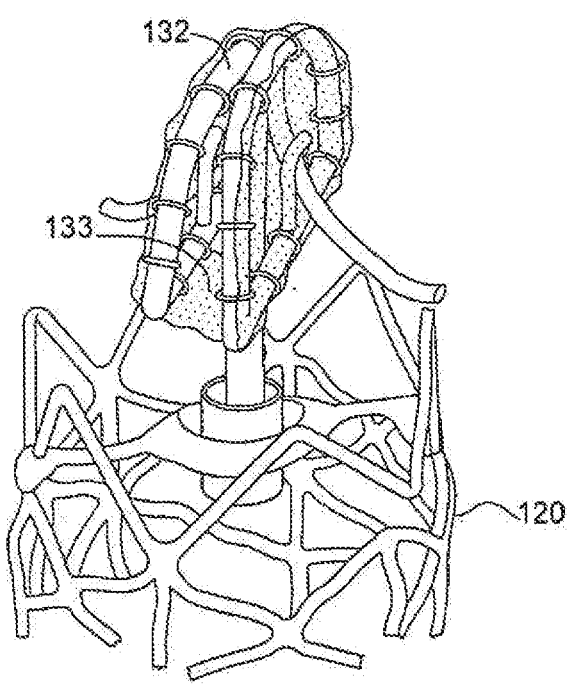
FIG. 2L is a partial perspective view of the bi-leaflet percutaneous heart valve of FIG. 2F mounted on the valve cage stent of FIG. 2I, with the valve in the open position.

Each part 132a and 132b of the frame 132 includes a slot 134 for receiving a hinge 135 having a shape when deployed that is similar to a lower-case "t", as shown in FIGS. 2D and 2E, having two aims 135a and 135b and a stem 135c. The slot 134 is formed unitarily with the frame 132. The "t"-shaped hinge 135 is stamped out of memory metal (for example, nitinol) sheeting so that it is deformable. The arms 135 and 135b of the hinge 135 have projections 135d at their ends, which function as stops for the leaflets. The stem 135c of the hinge 135 has a snap-on or screw-in mechanism 141 for attachment to a valve mount 142 (shown in FIGS. 2I-2L), as described below.

The tissue cover 133 (shown in FIG. 2B) is made, for example, of equine or bovine pericardium, or various synthetic materials, for example, or medical grade silicone, fabric, or other compressible, materials, and is configured to cover the two parts 132a and 132b of the frame 132 with their straight sides in spaced apart relation, with a central aperture 133a in the center for receiving the stem of the "t"-shaped hinge 135 and two side apertures 133b in alignment with the slots 134 for receiving the arms 135a and 135b of the hinge 135. The tissue cover 133 is sewn to each part 132a and 132b of the frame 132, as shown in FIGS. 2C and 2F-2H, and thus connects the two parts 132a and 132b of the frame 132 in spaced-apart relation.

As discussed in greater detail below, in use, the bi-leaflet valve 130 is detachably connected to a valve mount 142 (shown in FIGS. 2I and 2l) via the "t"-shaped hinge 135, as shown in FIGS. 2K-2N, 4D-4G, and 5G-5I. The valve mount 142 is also made from a memory metal so that it is collapsible. More specifically, the valve mount 142 has arms 142a and 142b on either side of a receptacle 142c, which are folded up vertically when the valve cage stent 120 is in its compressed (undeployed) condition, the ends of the arms 142a and 142b being affixed to the valve cage stent 120.

The detachable and collapsible bi-leaflet construction of the valve 130 enables the valve 130 in conjunction with its entire delivery system to be sized down so that it can be inserted percutaneously using a catheter, as described below.

Figure 3A:
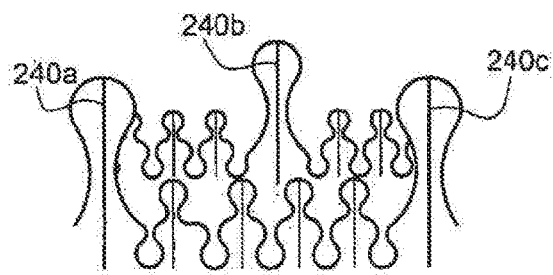
FIG. 3A is a diagrammatic perspective view of a frame for a tri-leaflet percutaneous heart valve in accordance with the present invention.
Figure 3B:
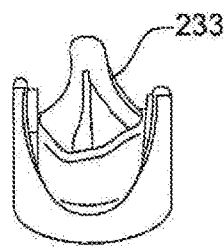
FIG. 3B is a perspective view of a tissue cover for the frame of FIG. 3A.
Figure 3C:
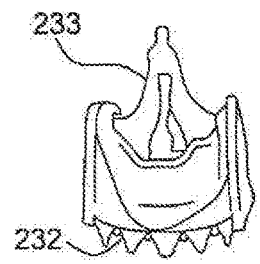
FIG. 3C is a perspective view of an assembled tri-leaflet percutaneous heart valve in accordance with the present invention, incorporating the frame of FIG. 3A and the tissue cover of FIG. 3B
Figure 3D:
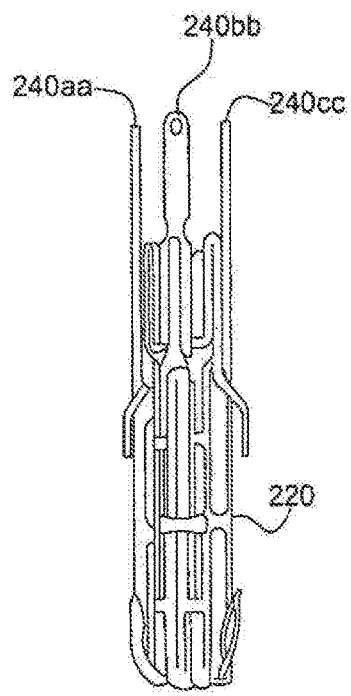
FIG. 3D is a side perspective view of the valve cage stent for use with the tri-leaflet percutaneous heart valve of FIG. 3C.
Figure 3E:
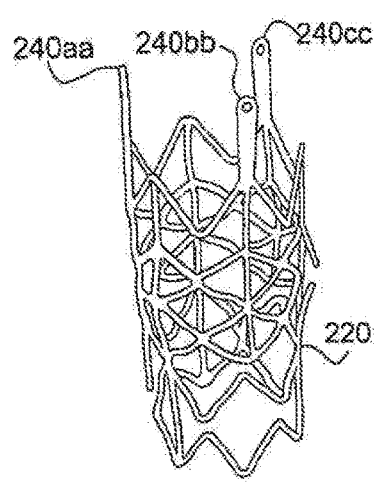
FIGS. 3E and 3F are top perspective views of the valve cage stent for use with the tri-leaflet percutaneous heart valve of FIG. 3C.
Figure 3F:
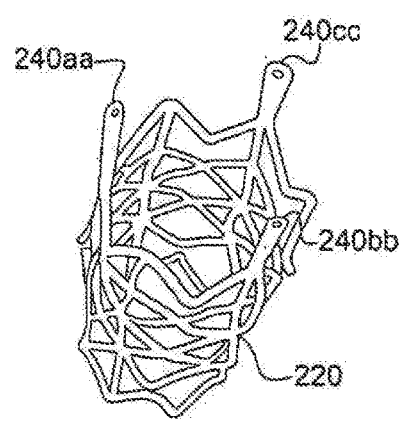

Referring now to FIGS. 3A-3C, the tri-leaflet tissue valve 230 comprises an expandable and compressible valve frame 232 (shown in FIG. 3A) made from a memory metal wire or strip and a tissue cover 233 (shown in FIGS. 3B and 3C). The tissue cover 233 is made from the individual cusps of a porcine aortic valve sewn to appropriate fabric. Three identical cusps are selected. Two or more pigs are used to get ideal sized aortic cusps. The muscle bar cusp is preferably not used; and all of the sinus and surrounding tissue is S discarded. The commissural height is maintained at all cost. The tissue cover 233 (that is, the cusps sewn to the fabric) is fitted and sewn to the valve frame 232. The valve frame 232 has three cannulated commissural posts 240a, 240b, and 240c mounted thereon, and the tissue cover 233 is sewn to the commissural posts 240a, 240b, and 240c to complete the tri-leaflet valve 230 (FIG. 3C).

As shown in FIGS. 3A-3C, the tri-leaflet valve 230 is mounted on commissural pins 240aa, 240bb, and 240cc provided on a valve cage stent 220 of the type disclosed in provisional application No. 60/735,221, which is incorporated herein by reference in its entirety. More specifically, the commissural posts 240a, 240b, and 240c of the valve frame 232 are cannulated to receive the commissural pins 240aa, 240bb, and 240cc, respectively, of the valve cage stent 220, thereby connecting the valve frame 232 (and thus the valve 230) to the valve cage stent 220. As described below, the heart valve prosthesis 210 incorporating the tri-leaflet valve 230 is delivered using a catheter.

Figure 3G:
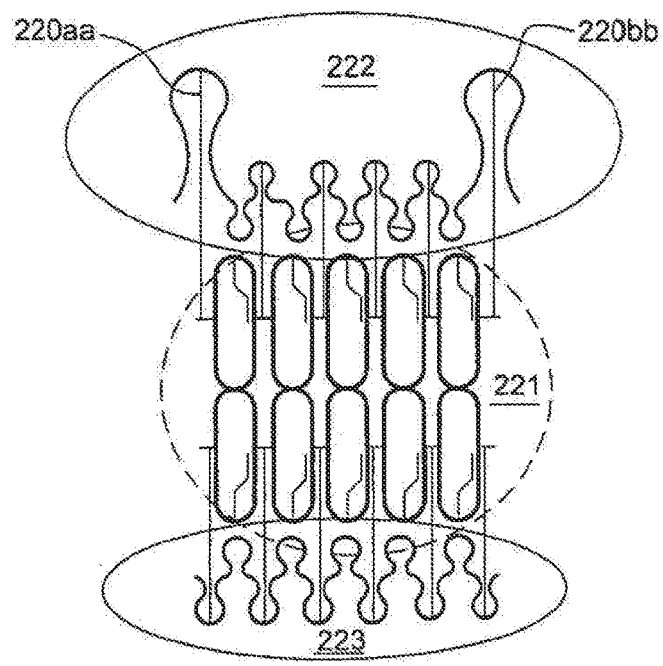
FIG. 3G is a diagrammatic view of a portion the valve cage stent for use with the tri-leaflet percutaneous heart valve of FIG. 3C, which as been opened up and flattened for purposes of illustration.
Figure 3H:
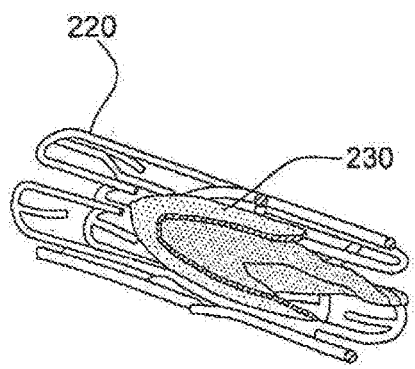
FIG. 3H is a partially cut-away perspective view of the tri-leaflet percutaneous heart valve of FIG. 3C mounted on the valve cage stent of FIG. 3D, in the undeployed condition.
Figure 3I:
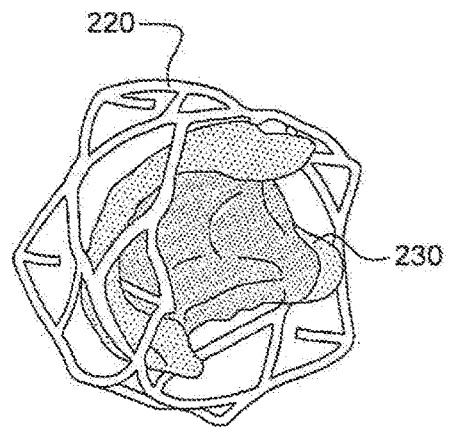
FIG. 3I is a partially cut-away perspective view of the tri-leaflet percutaneous heart valve of FIG. 3C mounted on the valve cage stent of FIG. 3D, in the deployed condition.

As shown in FIG. 3G, the valve cage stent 220 for use with the tri-leaflet valve 230 has three different zones 221, 222, and 223 along its longitudinal axis, the different zones having different geometric configurations so as to perform different functions. The first, or center, zone 221 functions as the stent connector, which is identical to the stent disclosed in Int'al Patent Application No. PCT/US2006/043526, filed Nov. 9, 2006 (which is based on U.S. Provisional Application No. 60/735,221), and which connects to the native valve annulus. The second and third zones 222 and 223, at either end of the center zone 221, function respectively as the superior valve rim carrying the commissural pins in the tri-leaflet valve prosthesis 210 or the valve mount in the bi-leaflet valve prosthesis 110, and the inferior valve skirt. The valve skirt 223 provides additional support, as well as a fabric/tissue attachment area to minimize leaking.

Figure 8:
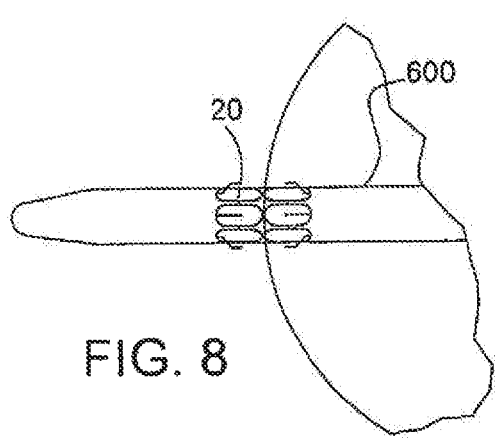
FIG. 8 is a side view of a valve cage stent mounted on a balloon catheter.
Figure 9A:
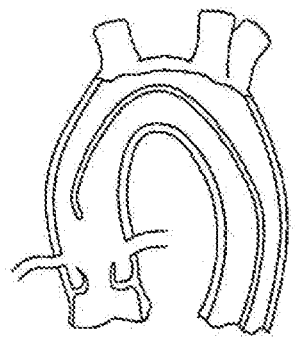
FIGS. 9A-9T show the sequence of steps in implantation of the tri-leaflet percutaneous heart valve of FIG. 3C in an aorta, in which the valve is attached to the valve cage stent within the delivery catheter.
Figure 9B:
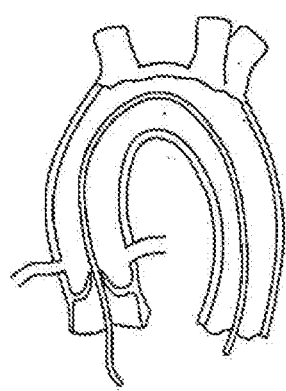
Figure 9C:
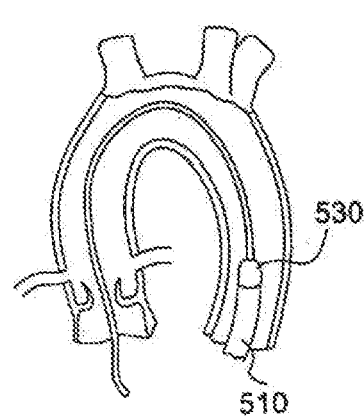
Figure 9D:
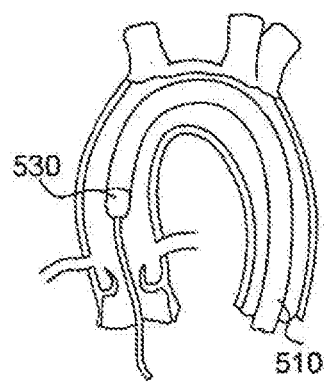
Figure 9E:
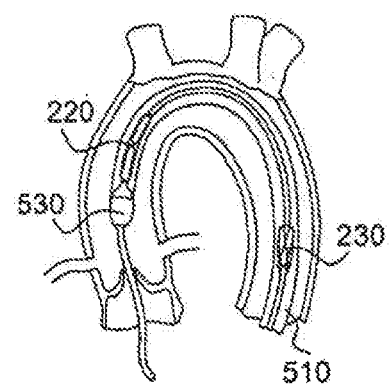
Figure 9F:
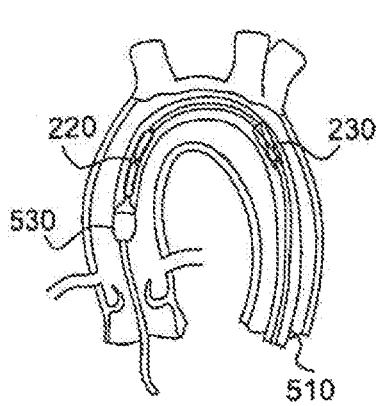
Figure 9G:
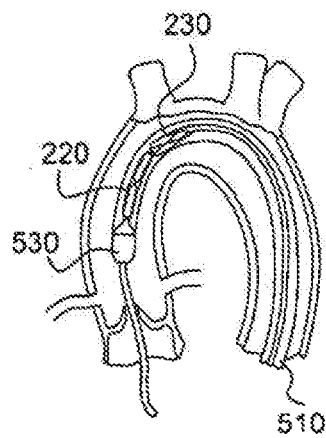
Figure 9H:
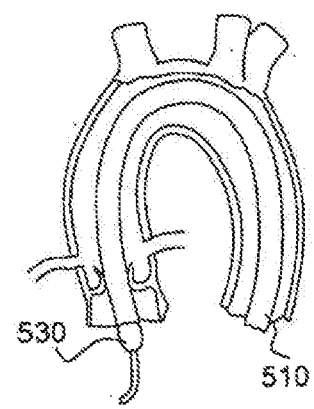
Figure 9I:
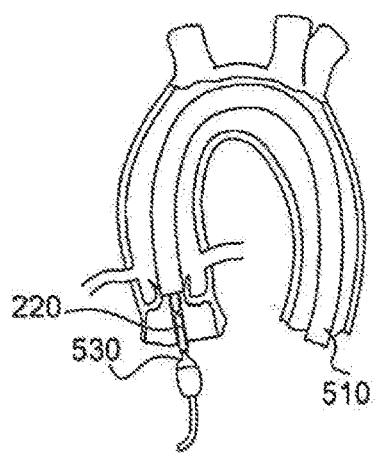
Figure 9J:
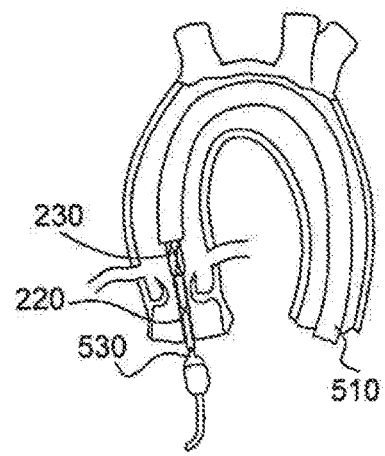
Figure 9K:
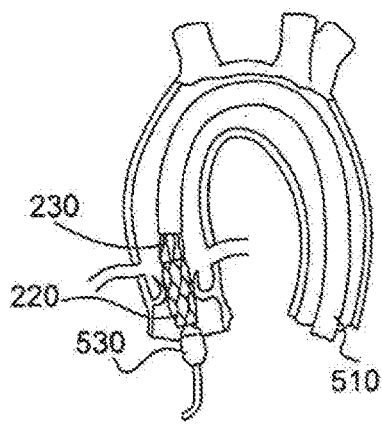
Figure 9L:
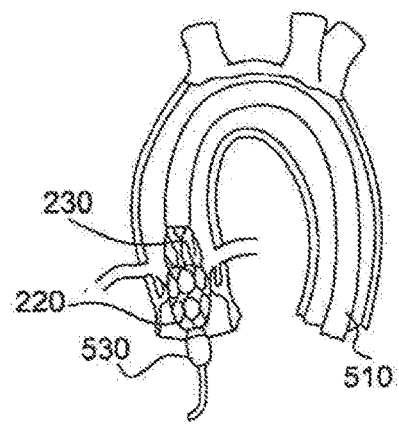
Figure 9M:
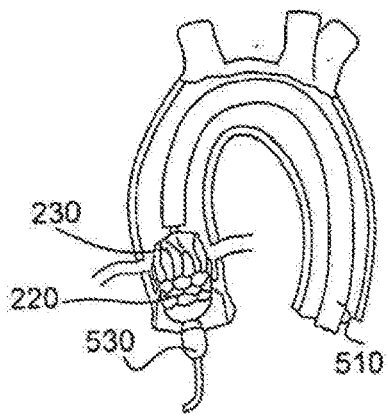
Figure 9N:
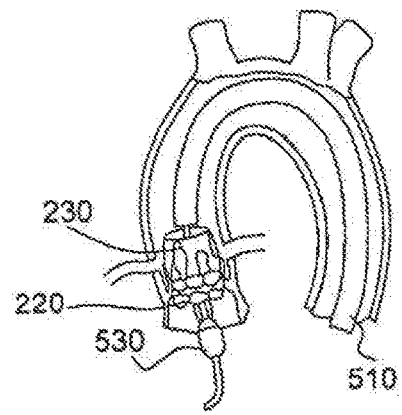
Figure 9O:
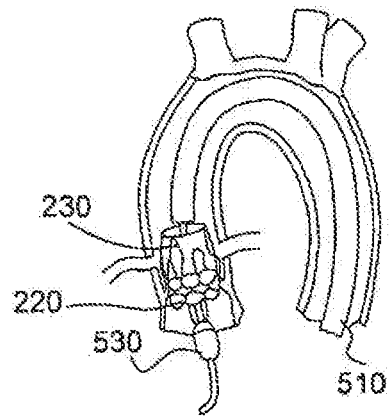
Figure 9P:
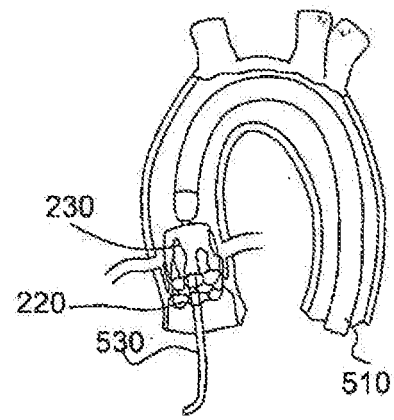
Figure 9Q:
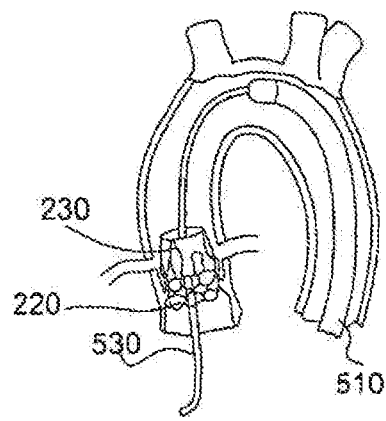
Figure 9R:
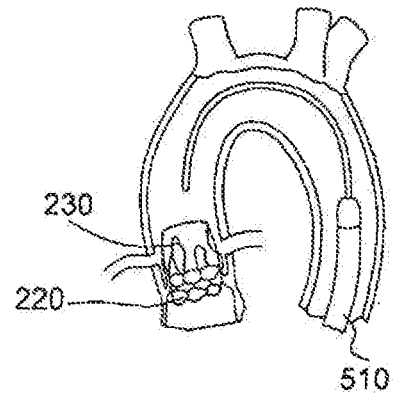
Figure 9S:
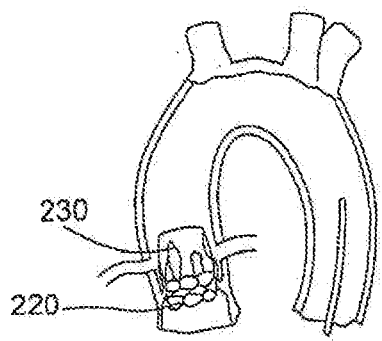
Figure 9T:
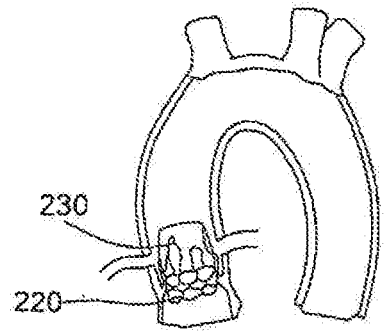

The present invention also encompasses a system and method for implanting the above-described percutaneous valve prostheses 10 in the body. In a first embodiment, the system comprises a valve cage stent 20 for implantation in the body by the use of a first catheter of a delivery system 500 (shown in FIGS. 8A and 8B, and as described in greater detail hereinafter) to provide a stable, fixed, and sturdy frame within which an elastic, compressible valve 30 can be inserted and secured by a second catheter (not shown), and the valve 30 is attached to the valve cage stent 20 after they are discharged from their respective catheters. Performing the procedure in two parts at the same session downsizes the devices considerably, so that the procedure can be performed percutaneously. In a second embodiment, the system comprises a valve cage stent 20 and an elastic, compressible valve 30 which are inserted using the same catheter, and the valve 30 is attached to the valve cage stent 20 within the catheter, as shown in FIGS. 9A-9T.

The valve cage stent 20 is a self-expanding or balloon expandable cylindrical valve cage stent 20, made from memory metal, or stainless steel respectively. The self-expanding valve cage stent and the balloon expandable valve cage stent are structurally the same (that is, they differ only in the material from which they are made). The valve cage stent 20 is fabricated from metal tubing (memory metal or stainless steel), so that it is cylindrical in shape, with the stent pattern being cut into the tubing by laser.

The expansion of the valve cage stent 20 produces maximal foreshortening of the ovals in the mid portion of the stent and thus provides active fixation of the stent to the annulus of the valve being replaced. The valve cage stent 20 has a fabric covering on its interior and parts of its exterior surfaces so in its expanded state it forms a complete seal and does not allow any leakage of blood.

For delivery, the valve cage stent 20 is mounted on a balloon 600 (FIG. 8), or in a restraining sheath if self-expandable. The delivery system apparatus 500 is shown in FIGS. 7A-7C. The delivery system apparatus 500 comprises a flexible outer sheath 510, in which the valve cage stent 20 is inserted with a first set of guide wires 520 attached thereto, followed by a slotted nosecone 530 having another set of guide wires 540 attached thereto.

Figure 6A:
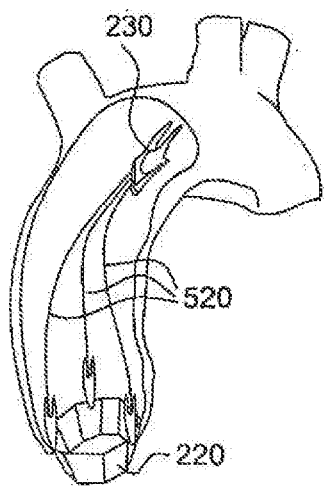
FIGS. 6A-6J show the sequence of steps in implantation of the tri-leaflet percutaneous heart valve of FIG. 3C in an aorta, in which the valve is attached to the valve cage stent outside the delivery catheter.
Figure 6B:
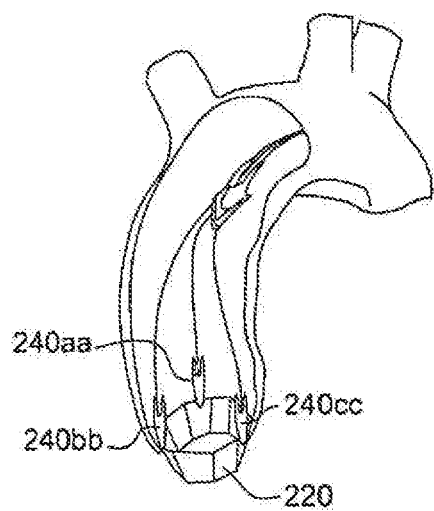
Figure 6C:
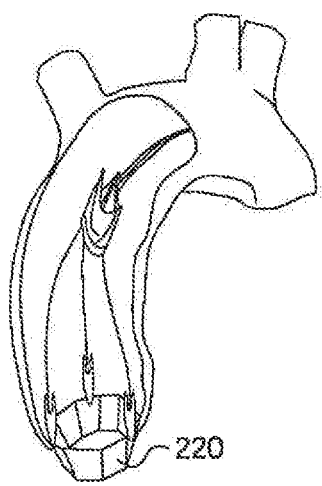
Figure 6D:
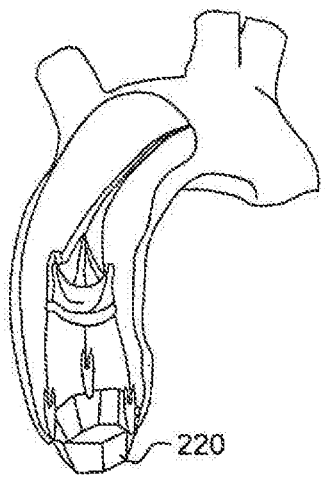
Figure 6E:
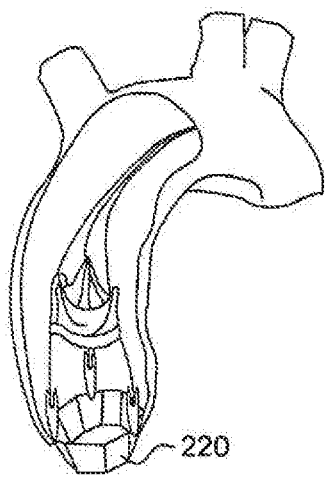
Figure 6F:
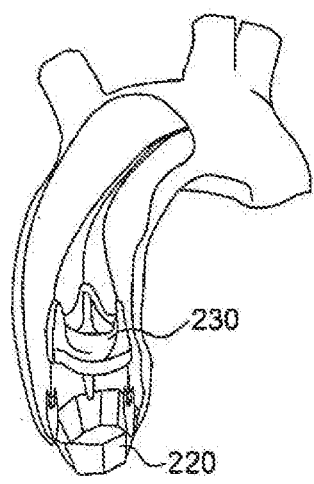
Figure 6G:
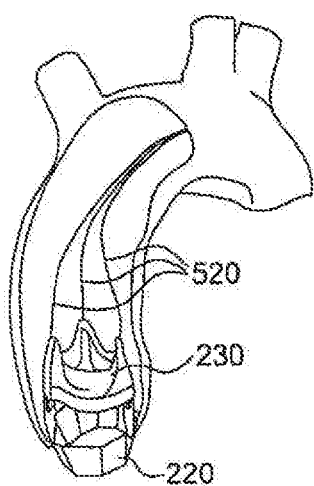
Figure 6H:
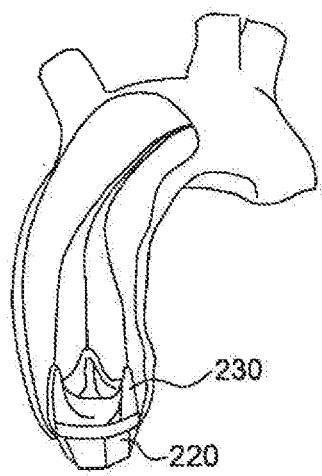
Figure 6I:
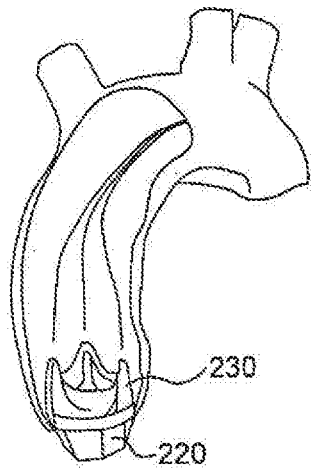
Figure 6J:
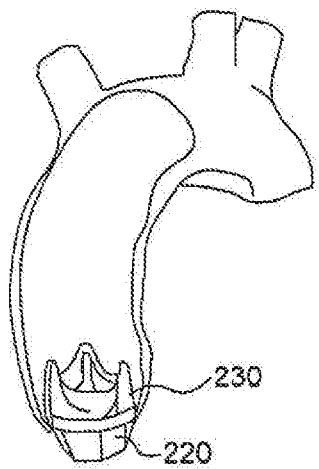

The valve cage stent 20 has provisions for the attachment of the prosthetic valve, depending on the type of prosthetic valve contemplated to be used. For example, in the case of a bi-leaflet valve, the valve is attached to the valve cage stent 120 via a valve mount affixed to the valve cage stent 120, as shown in FIGS. 4D-4G and 5G-5I. In the case of a tri-leaflet valve, the valve is attached to the valve cage stent 220 via engagement of the valve commissural posts 240*a*, 240*b*, and 240*c* with the commissural pins 240*aa*, 240*bb*, and 240*cc* of the valve cage stent 220, as shown in FIGS. 6H-6J.

Figure 4A:
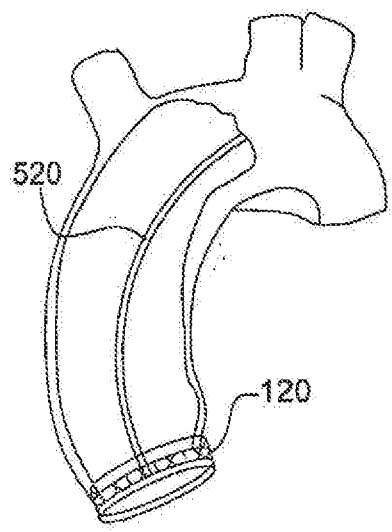
FIGS. 4A-4G show the sequence of steps in implantation of the bi-leaflet percutaneous heart valve prosthesis of FIG. 2C in an aorta, in which the valve is attached to the valve cage stent outside the delivery catheter.
Figure 4B:
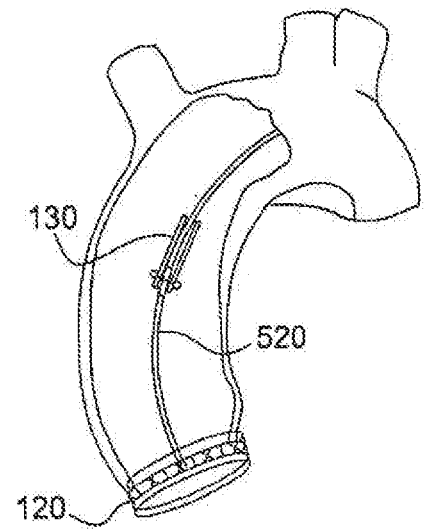
Figure 4C:
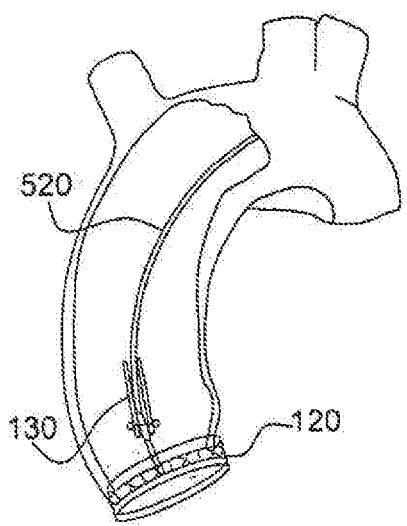
Figure 4D:
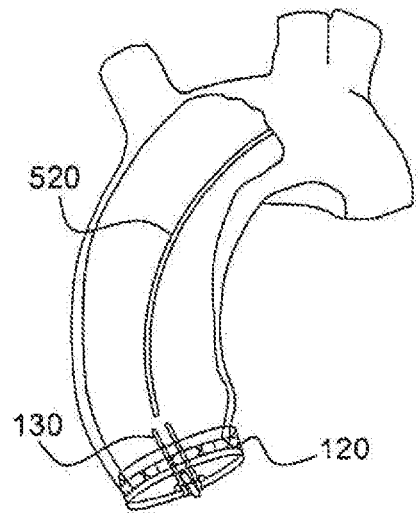
Figure 4E:
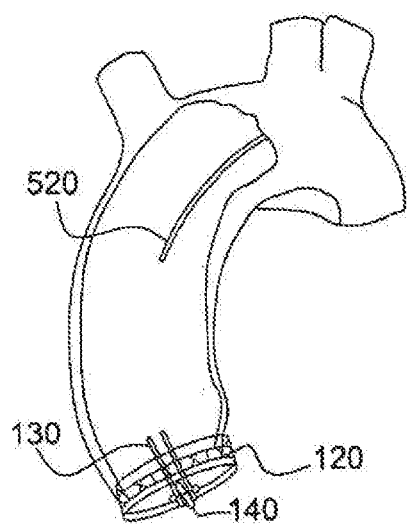
Figure 4F:
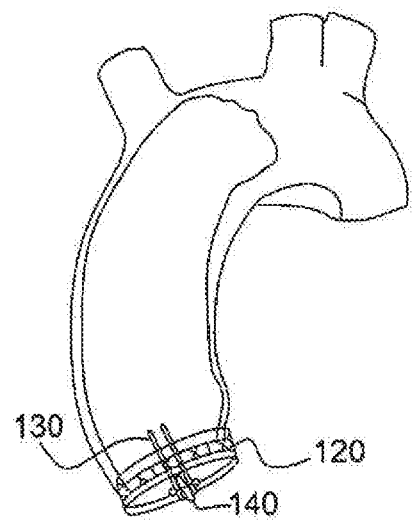
Figure 4G:
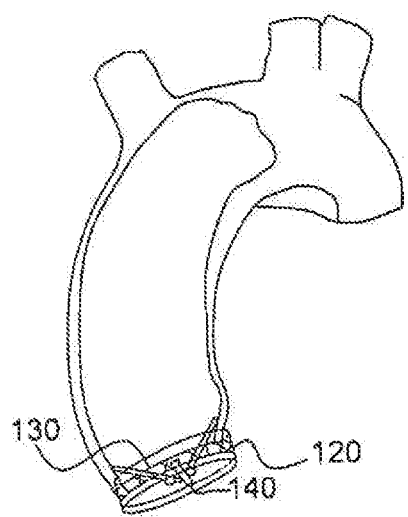
Figure 5A:
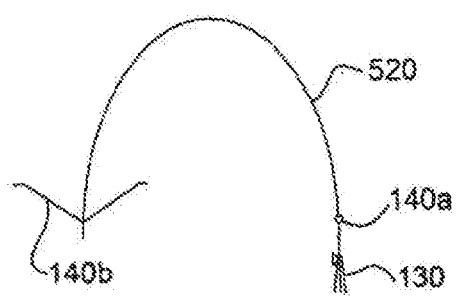
FIGS. 5A-5I are diagrammatic representations of the sequence of steps in implantation of the bi-leaflet percutaneous heart valve of FIG. 2C, the aorta being omitted from all of FIGS. 5A-5I and the valve cage being omitted from FIGS. 5A-5F for clarity.
Figure 5B:
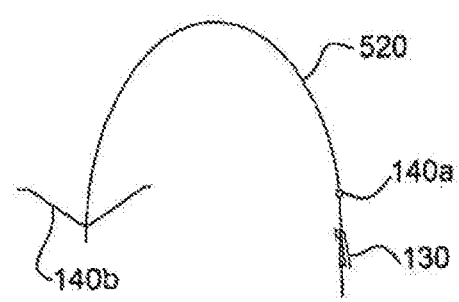
Figure 5C:
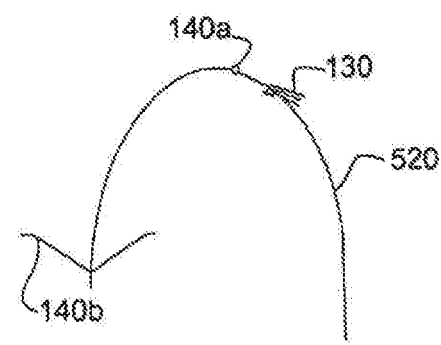
Figure 5D:
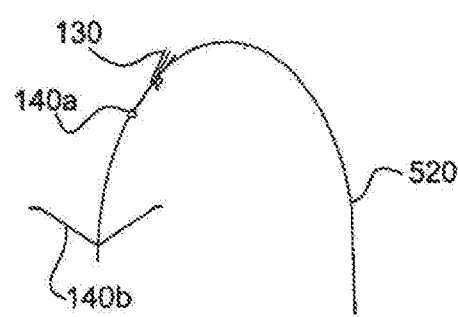
Figure 5E:
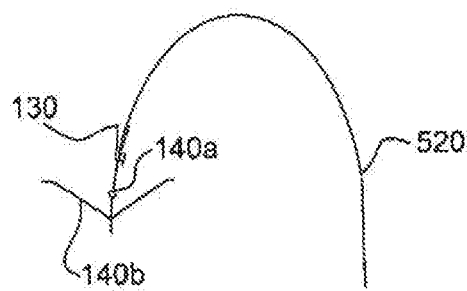
Figure 5F:
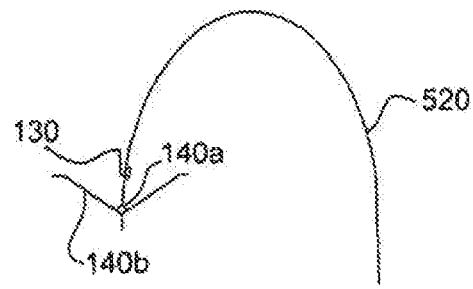
Figure 5G:
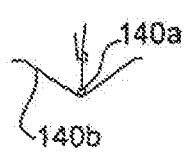
Figure 5H:
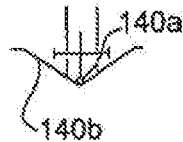
Figure 5I:
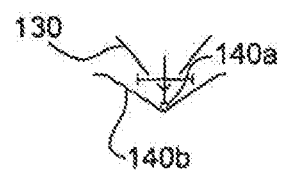

The delivery system employs a two stage procedure, both stages of which can be performed at the same session, only minutes apart. The first stage is insertion of the valve cage stent 20. In the case of a bi-leaflet valve, as shown in FIG. 4A, the valve cage stent 120 has a valve mount connected thereto and a guide wire connected to the valve mount. In the case of a tri-leaflet valve, as shown in FIGS. 6A-6G and as described above, the valve cage stent 220 has three commissural pins 240*aa*, 240*bb*, and 240*cc* provided thereon and guide wires connected thereto.

The second stage is insertion of the elastic and compressible valve, which is restrained in another catheter (not shown) for delivery into the valve cage stent 20. As shown in FIGS. 4A-4D, 5A-5F, and 6A-6H, in the second stage, the valve is placed over the guide wire (in the case of a bi-leaflet valve) or guide wires (in the case of the tri-leaflet valve) connected to the valve cage stent 20 in order to ensure proper positioning of the valve relative to the stent. Once the valve is seated, the guide wire or wires are withdrawn (FIGS. 4D-4G, 5G-5I, and 6I-6J).

Because the bi-leaflet valve is detachable from the valve mount, it can be replaced when necessary. The valve mount has a snap-on or screw-in mechanism for attachment of the "t"-shaped hinge 135 thereto, as well as the above-described guide wire attached to it for placement of the valve. The use of a valve cage 20 allows for fabrication of a tri-leaflet tissue valve.

In addition, the connection of valve 30 to the valve cage stent 20 provides the best effective flow dynamics, the flexibility of the whole system 500 is greatly increased, and the profile of the whole system 500 is reduced so that it can be inserted through a small opening in the access vessel.

Modifications and variations of the above-described embodiments of the present invention are possible, as appreciated by those skilled in the art in light of the above teachings. It is therefore to be understood that, within the scope of the appended claims and their equivalents, the invention may be practiced otherwise than as specifically described.

What is claimed is:

1. A method for delivering a heart valve prosthesis to a native valve annulus, comprising:
   delivering a self-expanding valve cage stent to the native valve annulus, the valve cage stent including opposing anchoring portions for engaging surrounding tissue and having a plurality of guide wires connected thereto and circumferentially spaced around a periphery thereof;
   expanding the valve cage stent within the native valve annulus;
   engaging tissue of the native valve annulus with the opposing anchoring portions, wherein the opposing anchoring portions extend radially outwardly from a longitudinal axis of the valve cage stent;
   positioning at least a portion of a tissue valve within the valve cage stent, the tissue valve comprising an expandable and compressible valve frame made from a memory metal, wherein proper positioning of the tissue valve with respect to the valve cage stent is ensured by guiding the tissue valve over the guide wires;
   once the tissue valve is positioned, removing the guide wires from the body; and
   expanding the tissue valve and coupling the tissue valve to the valve cage stent;
   wherein the valve cage stent is implanted by use of a first catheter to provide a stable support structure and wherein the tissue valve is implanted within the valve cage stent by use of a second catheter.

2. The method of claim 1, wherein the valve cage stent comprises a tubular structure formed by a plurality of struts.

3. The method of claim 1, wherein the tissue valve comprises three commissure posts.

4. The method of claim 3, wherein the valve cage stent comprises three commissure pins along an outlet portion, the commissure pins shaped for connecting to the commissure posts of the tissue valve.

5. The method of claim 4, wherein the commissure posts are cannulated for receiving the commissure pins.

6. The method of claim 1, wherein the tissue valve further comprises a tissue cover.

7. The method of claim 1, wherein the tissue valve further comprises a fabric cover to provide additional support and minimize leaking.

8. The method of claim 1, wherein the valve cage stent is substantially cylindrical.

9. The method of claim 1, wherein the valve cage stent is formed by cutting a tube with a laser.

10. The method of claim 1, wherein the valve cage stent further comprises fabric along at least a portion of an interior surface and an exterior surface.

11. The method of claim 1, wherein the first catheter includes a flexible outer sheath for restraining the valve cage stent.

12. The method of claim 1, wherein the tissue valve is a tri-leaflet tissue valve.

13. The method of claim 1, wherein the heart valve prosthesis is an aortic valve prosthesis.

14. The method of claim 1, wherein the tissue valve is coupled to a superior rim of the valve cage stent.

15. A method for delivering a heart valve prosthesis to a native valve annulus, comprising:
   delivering a self-expanding valve cage stent to the native valve annulus, the valve cage stent including opposing anchoring portions for engaging surrounding tissue, the valve cage stent further comprising three commissure pins along an outlet portion;
   expanding the valve cage stent within the native valve annulus;
   engaging tissue of the native valve annulus with the opposing anchoring portions, wherein the opposing anchoring portions extend radially outwardly from a longitudinal axis of the valve cage stent;
   positioning at least a portion of a tissue valve within the valve cage stent, the tissue valve comprising an expandable and compressible valve frame made from a memory metal, wherein the tissue valve comprises three commissure posts; and
   expanding the tissue valve and coupling the tissue valve to the valve cage stent, wherein the commissure pins of the valve cage stent are shaped for connecting to the commissure posts of the tissue valve;
   wherein the valve cage stent is implanted by use of a first catheter to provide a stable support structure and wherein the tissue valve is implanted within the valve cage stent by use of a second catheter.

16. The method of claim 15, wherein the commissure posts are cannulated for receiving the commissure pins.

17. The method of claim 15, wherein the tissue valve further comprises a fabric cover to provide additional support and minimize leaking.

18. The method of claim 17, wherein the tissue valve is a tri-leaflet tissue valve.

19. The method of claim 17, wherein the valve cage stent further comprises fabric along at least a portion of an interior surface and an exterior surface.

* * * * *